United States Patent [19]

George et al.

[11] Patent Number: 5,210,086

[45] Date of Patent: May 11, 1993

[54] 2-AMINOPYRIMIDINE-4-CARBOXAMIDE DERIVATIVES, THEIR PREPARATION AND THEIR USE IN THERAPY

[75] Inventors: Pascal George, St. Arnoult en Yvelines; Christian Maloizel, Meudon; Benoit Marabout, Massy, all of France

[73] Assignee: Synthelabo, Paris, France

[21] Appl. No.: 769,218

[22] Filed: Oct. 1, 1991

[30] Foreign Application Priority Data

Oct. 2, 1990 [FR] France ................................ 90 12094

[51] Int. Cl.$^5$ ................... A61K 31/505; C07D 239/02
[52] U.S. Cl. ................................. 514/275; 544/330; 544/332
[58] Field of Search ................. 544/330, 332; 514/275

[56] References Cited

U.S. PATENT DOCUMENTS

| | | | |
|---|---|---|---|
| 4,031,221 | 6/1977 | Helsley et al. | 424/267 |
| 4,853,387 | 8/1989 | Manoury et al. | 544/332 |

FOREIGN PATENT DOCUMENTS

| | | | |
|---|---|---|---|
| 0435749 | 7/1991 | European Pat. Off. | 544/332 |
| 1964515 | 7/1970 | Fed. Rep. of Germany . | |
| 2549999 | 5/1977 | Fed. Rep. of Germany . | |
| 2737630 | 11/1987 | Fed. Rep. of Germany . | |
| 2010615 | 2/1970 | France . | |
| 1203149 | 8/1970 | United Kingdom . | |

OTHER PUBLICATIONS

Balsamo, A. et al., "3-[(2-Ethoxyphenoxy)methyl]-piperidine Derivatives. Synthesis and Antidepressant Activity", J. Med. Chem. 1987, 30, 222-225.

Daves, G., Jr. et al., "Pyrimidines. XIII. 2- and 6-Substituted 4-Pyrimidinecarboxylic Acids (la)", J. Het. Chem. (1964), 1, 130-133.

Boswell, Robert, Jr. et al., "Synthesis of Some N-Carboxylic Acid Derivatives of 3-Phenoxypyrrolidines, 4-Phenoxypiperidinies, and 3-Phenoxynortropanes with Muscle Relaxant and Anticonvulsant Activities", J. Med. Chem., 1974, vol. 17, No. 9.

Glennon, R. A. et al., "N-(Phthalimidoalkyl) Derivatives of Serotonergic Agents: A Common Interaction at 5-HT$_{1A}$ Serotonin Binding Sites?", J. Med. Chem, 1989, 32, 1921-1926.

Nishikawa, Y. et al., "Acrylamide Derivatives as Antiallergic Agents. I. Synthesis and Structure-Acitivty Relationships of N-[(4-Substituted 1-piperazinyl)alkyl-]-3-(aryl and heteroaryl)acrylamides", Chem. Pharm. Bull. 37(1) 100-105 (1989).

*Primary Examiner*—Mukund J. Shah
*Assistant Examiner*—Y. N. Gupta
*Attorney, Agent, or Firm*—Jacobson, Price, Holman & Stern

[57] ABSTRACT

A compound which is a 2-aminopyrimidine-4-carboxamide derivative, of the general formula (I)

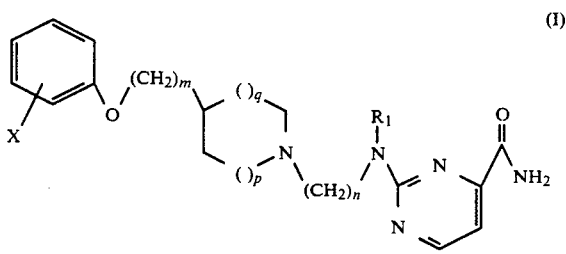

in which
m is 0 or 1,
p is 0 or 1,
q is 1 or 2,
n is 2 or 3,
$R_1$ represents a hydrogen atom or a methyl group, and
X represents at least one substituent selected from hydrogen, fluorine, chlorine, methoxy, methyl, isopropyl, or a pharmaceutically acceptable addition salt thereof, its preparation and use in therapy.

5 Claims, No Drawings

2-AMINOPYRIMIDINE-4-CARBOXAMIDE DERIVATIVES, THEIR PREPARATION AND THEIR USE IN THERAPY

The present invention relates to a compound which is a 2-aminopyrimidine-4-carboxamide derivative, to its preparation and to its use in therapy.

The present invention provides a compound which is a 2-aminopyrimidine-4-carboxamide derivative of the formula (I)

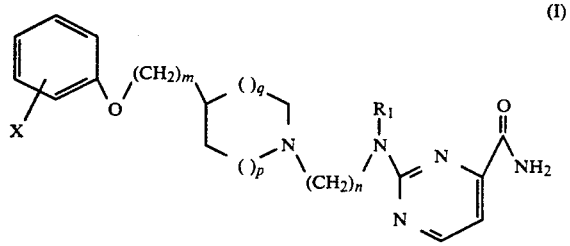

in which
m is 0 or 1;
p is 0 or 1;
q is 1 or 2;
n is 2 or 3;
$R_1$ represents a hydrogen atom or a methyl group; and X represents at least one substituent selected from hydrogen, fluorine, chlorine, methoxy, methyl and isopropyl;
or a pharmaceutically acceptable acid addition salt thereof.

In a preferred embodiment of the invention the sum of p and q is equal to two.

In another preferred embodiment of the invention the pharmaceutically acceptable acid addition salt is the fumarate, hemifumarate, hydrated fumarate or hydrochloride.

Examples of specific compounds of the present invention are:

2-[{3-[4-(4-fluorophenoxy)-1-piperidyl]propyl}amino]-pyrimidine-4-carboxamide or the fumarate thereof;

2-[{3-[3-(phenoxymethyl)-1-piperidyl]propyl}amino]-pyrimidine-4-carboxamide or the fumarate thereof;

2-{[3-{3-[(4-fluorophenoxy)methyl]-1-piperidyl}propyl]amino}pyrimidine-4-carboxamide or the fumarate thereof;

2-[{3-[4-{[5-methyl-2-(1-methylethyl)phenoxy]methyl}-1-piperidyl]propyl}amino]pyrimidine-4-carboxamide or the fumarate thereof;

2-{[3-{4-[(5-chloro-2-methoxyphenoxy)methyl]-1-piperidyl}propyl]amino}pyrimidine-4-carboxamide or the hydrated fumarate thereof;

2-{[3-{4-[(4,5-difluoro-2-methoxyphenoxy)methyl]-1-piperidyl}ethyl]amino}pyrimidine-4-carboxamide or the fumarate thereof; and

[N-{2-[4-(4-fluorophenoxy)-1-piperidyl]ethyl}-N-methylamino]pyrimidine-4-carboxamide or the fumarate thereof.

The compounds of the invention may be in the form of racemic mixtures or pure enantiomers.

The present invention further provides a process for the preparation of a compound which is a 2-aminopyrimidine-4-carboximide or a pharmaceutically acceptable acid addition salt thereof which process comprises reacting a phenoxypiperidine of formula (II) wherein X, m, p and q are as hereinbefore defined, optionally in hydrochloride form, with a halogenated reagent of formula (III) wherein $R_1$ and n are as hereinbefore defined, Y represents a halogen atom, and R represents an amino-protective group, for example a triphenylmethyl group, or R forms together with $R_1$ a protective group such as a phthalimido group [as described in J. Med. Chem (1989), 32(8), 1921–1926 and Chem. Pharm. Bull (1989), 37(1), 100–105)] in an aprotic solvent such as dimethylformamide (DMF), in the presence of an organic base such as triethylamine (TEA) or an inorganic base such as potassium carbonate ($K_2CO_3$), preferably at a temperature of from 40° to 100° C., to obtain a diamine of formula (IV) followed by a deprotection step to form an amine of formula (V) which is then reacted with 2-chloropyrimidine-4-carboxamide of formula (VI), in an aprotic solvent, for example DMF, in the presence of a base, for example $K_2CO_3$, at a temperature of 20° to 40° C., to yield a 2-aminopyrimidine-4-carboxamide derivative of formula (I) and then, if desired converting said derivative into an acid addition salt in a manner known per se.

In the case where R is a triphenylmethyl group, the deprotection step is generally performed using gaseous hydrochloric acid in an aliphatic alcohol, for example methanol, at a temperature of 0° to 60° C.; in the case where R and $R_1$ together form a phthalimido group, a deprotection step similar to that described in the literature cited above, for example with hydrazine, may be performed.

The process of the present invention is illustrated by reaction Scheme 1 given below.

Scheme 1

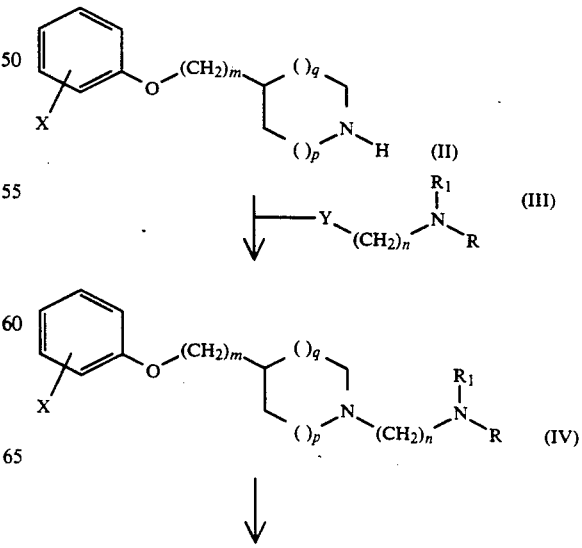

-continued
Scheme 1

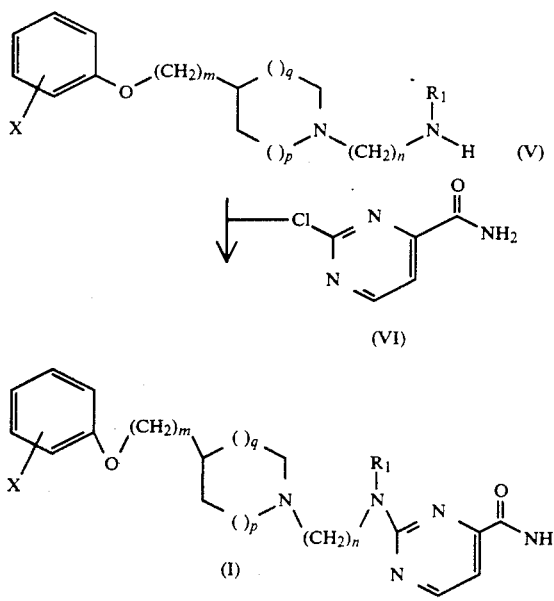

The phenoxypiperidine (II) may be obtained by methods similar to those described in U.S. Pat. No. 4,031,221, J. Med. Chem. (1974) 17(9) 1000–1008 and DE 1,964,515. A phenoxymethylpiperidine (II) may be prepared by methods similar to those described in J. Med. Chem. (1987) 30(1) 222–5 and DE 2,737,630, DE 2,549,999, GB 1,203,149 and FR 2,010,615.

The halogenated reagent of formula (III) wherein R represents a triphenylmethyl groups (a ω-halo-N-(triphenylmethyl)alkylamine), and 2-chloropyrimidine-4-carboxamide are described in FR 89/17,304.

The halogenated reagent of formula (III) is either commercially available when $R_1$ and R together form a phthalimido group, or, when $R_1$ is H or $CH_3$, may be prepared according to Scheme 2 given below, according to which an ω-haloalkylamine of formula (VII) is reacted with a compound of formula RCl, wherein R is as hereinbefore defined, for example trityl chloride, in a halogenated inert solvent such as dichloromethane, in the presence of an organic base such as triethylamine, at a temperature of from 20° to 80° C.

Scheme 2

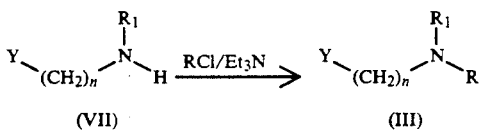

2-Chloropyrimidine-4-carboxamide of formula (VI) may be prepared according to Scheme 3, given below, from 2-chloropyrimidine-4-carbonitrile of formula (VIII) by treatment with gaseous hydrochloric acid in formic acid. 2-Chloropyrimidine-4-carbonitrile may also be prepared according to the method described in J. Het. Chem. (1964), 1, 130–133.

Scheme 3

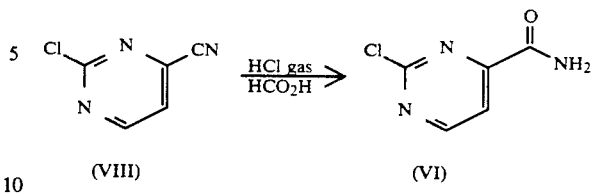

The following examples illustrate the preparation of compounds according to the present invention.

Elemental microanalyses and the IR and NMR spectra confirm the structures of the products obtained.

EXAMPLE 1

2-[{3-[4-(4-Fluorophenoxy)-1-piperidyl]propyl}amino]-pyrimidine-4-carboxamide fumarate 1.1.
2-{3-[4-(4-Fluorophenoxy)-1-piperidyl]propyl}-1H-isoindole-1,3(2H)-dione 9.26 g (0.04 mol) of 4-(4-fluorophenoxy)piperidine hydrochloride, 10.72 g (0.04 mol) of 3-bromopropyl-N-phthalimide and 13.89 g (0.1 mol) of $K_2CO_3$ in 90 ml of DMF are reacted for 3 h at 100° C.

The reaction mixture is poured into ice-cold water. It is extracted 3 times with AcOEt and the organic phase is then washed 3 times with water and then once with water saturated with NaCl. The solution is dried over $MgSO_4$, filtered and concentrated. The compound is obtained. Yield: 100%.

1.2. 4-(4-Fluorophenoxy)-1-piperidinepropanamine 13.8 g (0.04 mol) of 2-{3-[4-(4-fluorophenoxy)-1-piperidyl]propyl}-1H-isoindole-1,3(2H)-dione and 3.9 ml (0.08 mol) of hydrazine in 280 ml of EtOH are reacted for 3 h at the refluxing temperature, and the mixture is then left overnight. 15 ml of concentrated HCl and 20 ml of $H_2O$ are then introduced. The mixture is left for 3 hours at the refluxing temperature, then filtered and concentrated. The residue is taken up with water, filtered and rinsed with water. The filtrate is washed twice with ether, then alkalinised with NaOH and extracted 3 times with $CH_2Cl_2$. The solution is dried over $Na_2SO_4$, filtered and concentrated.

The compound is obtained. Yield: 86%.

1.3.
2-[{3-[4-(4-Fluorophenoxy)-1-piperidyl]-propyl}amino]pyrimidine-4-carboxamide 3.8 g (0.015 mol) of 4-(4-fluorophenoxy)-1-piperidine-propanamine, 2.36 g (0.015 mol) of 2-chloropyrimidine-4-carboxamide and 2.07 g (0.0225 mol) of $K_2CO_3$ in 80 ml of DMF are reacted. The mixture is stirred for 48 h at room temperature. It is poured into ice-cold water and extracted 3 times with ethyl acetate (AcOEt). The organic phase is washed 3 times with water, then dried over $MgSO_4$, filtered and concentrated.

5 g (0.0133 mol) of base are obtained, which base is taken up in an $EtOH + CH_2Cl_2$ mixture and a solution of 1.55 g (0.0133 mol) of fumaric acid in 200 ml of EtOH is added. The mixture is concentrated to ⅓ and then left to crystallise. Yield 61%. M.p. 171°–174° C.

EXAMPLE 2

2-[{3-[3-(Phenoxymethyl)-1-piperidyl]-propyl}amino]-pyrimidine-4-carboxamide fumarate

2.1.
2-{3-[3-(Phenoxymethyl)-1-piperidyl]propyl}-1H-isoindole-1,3(2H)-dione 6.8 g (0.03 mol) of 3-(phenoxymethyl)piperidine hydrochloride, 8 g (0.03 mol) of 3-bromopropyl-N-phthalimide and 10.4 g (0.075 mol) of $K_2CO_3$ dissolved in 85 ml of DMF are introduced into a 150-ml three-necked round-bottomed flask.

The mixture is stirred at 100° C. for 2 h.

It is poured into ice-cold water and extracted 3 times with AcOEt, and the organic phase is then washed 3 times with water and a final time with water saturated with NaCl.

The solution is dried over $MgSO_4$, filtered and concentrated.

12 g of oil are obtained (100% yield).

2.2. 3-(Phenoxymethyl)-1-piperidinepropanamine 2.9 ml (0.06 mol) of hydrazine are added to 11.3 g (0.03 mol) of 2-{3-[3-(phenoxymethyl)-1-piperidyl]-propyl}-1H-isoindole-1,3(2H)-dione in 226 ml of EtOH. The mixture is heated to the refluxing temperature while stirring for 3 h. It is left to cool and filtered, the filter is rinsed with EtOH and the filtrate is concentrated. The residue is taken up with ether. The filtrate is concentrated and 4.6 g of yellow oil are obtained.

The two insoluble portions are taken up in 100 ml of $H_2O$ and 25 ml of concentrated HCl. The mixture is heated to reflux while stirring for 2 h 30 min. The solution is left to cool. It is filtered, the filter is rinsed with a little water and the whole phase is then alkalinised with NaOH (caustic soda). It is extracted 3 times with ether and the organic phase is washed once with water. The solution is dried over $Na_2SO_4$, then filtered and concentrated. 2.3 g of oil are obtained.

2.3.
2-[{3-[3-(Phenoxymethyl)-1-piperidyl]propyl}amino]-pyrimidine-4-carboxamide 3.45 g (0.0147 mol) of 3-(phenoxymethyl)-1-piperidinepropanamine, 2.32 g (0.0147 mol) of 2-chloropyrimidine-4-carboxamide and 3 g (0.022 mol) of $K_2CO_3$ in 35 ml of DMF are introduced into a 250-ml round-bottomed flask.

The mixture is stirred at room temperature for 48 h. It is poured into water and extracted 3 times with AcOEt. The organic phase is washed 4 times with water and the solution is dried over $MgSO_4$, filtered and concentrated. The oil obtained is taken up with ether and the mixture is filtered.

5.3 g (0.0143 mol) of base are obtained, which base is taken up in a little EtOH. A solution of 1.66 g (0.0143 mol) of fumaric acid dissolved in 200 ml of ethanol is added. The mixture is concentrated almost to dryness and a little ether is then added. The product crystallises. It is filtered off and recrystallised in EtOH. Yield: 66%.
M.p. 144°–146° C.

EXAMPLE 3

2-{[3-{3-[(4-Fluorophenoxy)methyl]-1-piperidyl} propyl]amino}pyrimidine-4-carboxamide fumarate

3.1.
3-[(4-Fluorophenoxy)methyl]-N-(triphenylmethyl)-1-piperidinepropanamine 6.14 g (0.025 mol) of 3-[(4-fluorophenoxy)methyl]-piperidine hydrochloride, 10.46 g (0.0275 mol) of 3-bromo-N-triphenylmethylpropanamine and 8.64 g (0.0625 mol) of potassium carbonate in 50 ml of DMF are reacted.

The reaction mixture is heated to 90°–95° C. for 7 h 30 min. The reaction mixture is cooled to room temperature, poured into 150 ml of water and extracted with 3 times 100 ml of AcOEt. The organic phases are combined, washed with water and dried. The combined organic phases are filtered and evaporated. The product is obtained after chromatography.

3.2.
3-[(4-Fluorophenoxy)methyl]-1-piperidinepropanamine hydrochloride 9.9 g (0.0195 mol) of 3-[(4-fluorophenoxy)methyl]-N-(triphenylmethyl)-1-piperidinepropanamine are suspended in 300 ml of methanol, and gaseous hydrochloric acid is bubbled in for 20 min while the reaction mixture is cooled with an ice/salt/water mixture. The reaction mixture is heated to the refluxing temperature for 5 h and then cooled to room temperature. It is evaporated and filtered. After recrystallisation and drying, 5.81 g of product are obtained.
M.p. 130°–134° C.

3.3.
2-{[3-{3-[(4-Fluorophenoxy)methyl]-1-piperidyl} propyl]}amino}pyrimidine-4-carboxamide 5.09 g (0.015 mol) of 3-[(4-fluorophenoxy)methyl]-1-piperidinepropanimine hydrochloride, 2.36 g of 2-chloropyrimidine-4-carboxamide, 7.26 g (0.0525 mol) of $K_2CO_3$ and 0.2 g of sodium iodide are suspended in 450 ml of DMF. The reaction mixture is stirred under argon for 21 h, poured into 200 ml of water and extracted 3 times with ethyl acetate. The organic phase is washed with water, dried, filtered and evaporated. 3.35 g of product are obtained, which product is reacted with 1 g of fumaric acid in an ethanol/ethyl ether mixture. The fumarate is recrystallised in ethanol. Yield: 51.65%.
M.p. 150°–153° C.

EXAMPLE 4

2-[{3-[4-{[5-Methyl-2-(1-methylethyl)phenoxy]methyl}-1-piperidyl]-propyl}amino]pyrimidine-4-carboxamide fumarate

4.1.
4-{[5-Methyl-2-(1-methylethyl)phenoxy]methyl}-N-(triphenylmethyl)-1-piperidinepropanamine 11.35 g (0.04 mol) of 4-{[5-methyl-2-(1-methylethyl)-phenoxy]methyl}piperidine hydrochloride, 10.72 g (0.04 mol) of 3-bromopropyl-N-phthalimide and 13.8 g (0.1 mol) of $K_2CO_3$ in 113 ml of DMF are reacted. The mixture is stirred for 3 h at 100° C. It is poured into ice-cold water. The solution is extracted with AcOEt and then washed with water. It is dried, filtered and concentrated.

4.2.
4-{[5-Methyl-2-(1-methylethyl)phenoxy]methyl}-1-piperidinepropanamine hydrochloride 17.35 g (0.04 mol) of 4-{[5-methyl-2-(1-methylethyl)-phenoxy]methyl}-N-(triphenylmethyl)-1-piperidine-propanamine in 340 ml of EtOH are reacted with 3.9 ml (0.08 mol) of hydrazine. The mixture is brought to the refluxing temperature for 3 h. It is filtered, the filter is rinsed with a little EtOH, the filtrate is concentrated and the residue is then taken up in ether. Some insoluble matter is again filtered off. The filtrate is concentrated. The insoluble matter is combined in a round-bottomed flask and 25 ml of concentrated HCl and 75 ml of water are added. While stirring, the mixture is brought to reflux for 2 h. It is allowed to cool and then filtered, the filter is rinsed with water and the filtrate is then alkalinised with concentrated NH$_4$OH and extracted 3 times with ether. The solution is dried over Na$_2$SO$_4$, filtered and concentrated. The compound is obtained. Yield: 95%.

4.3.
2-[{3-[4-{[5-Methyl-2-(1-methylethyl)phenoxy]methyl}-1-piperidyl]-propyl}amino]pyrimidine-4-carboxamide 4.4 g (0.0144 mol) of 4-{[5-methyl-2-(1-methylethyl)-phenoxy]methyl}-1-piperidinepropanamine hydrochloride, 2.27 g (0.0144 mol) of 2-chloropyrimidine-4-carboxamide and 2.98 g (0.0216 mol) of K$_2$CO$_3$ in 86 ml of DMF are reacted.

The mixture is stirred for 48 h. It is poured into water and then extracted 3 times with AcOEt. The organic phase is washed 3 times with water. It is dried over Na$_2$SO$_4$, filtered and concentrated. The product crystallises.

It is taken up in a little ether and the mixture is filtered. 4.5 g (0.0105 mol) of base are obtained, which base is taken up in 100 ml of EtOH and a solution of 1.22 g (0.0105 mol) of fumaric acid in 150 ml of EtOH is added. M.p. 183°-88° C. Yield: 36%.

EXAMPLE 5

Hydrated
2-{[3-{4-[(5-chloro-2-methoxyphenoxy)methyl]-1-piperidyl}propyl]amino}pyrimidine-4-carboxamide furamate

5.1.
4-[(5-Chloro-2-methoxyphenoxy)methyl]-N-(triphenylmethyl)-1-piperidinepropanamine 5.85 g (0.020 mol) of 4-[(5-chloro-2-methoxyphenoxy)methyl]piperidine hydrochloride, 8.37 g (0.022 mol) of 3-bromo-N-(triphenylmethyl)propanamine and 6.91 g (0.050 mol) of K$_2$CO$_3$ in 50 ml of DMF are reacted. The reaction mixture is heated to 95°-100° C. It is cooled to room temperature, poured into 150 ml of water and extracted 3 times with ethyl acetate. The organic phases are combined, washed with water, dried over MgSO$_4$, filtered and evaporated. The product is obtained after chromatography.

5.2.
4-[(5-Chloro-2-methoxyphenoxy)methyl]-1-piperidinepropanamine hydrochloride 9.5 g (0.017 mol) of 4-[(5-chloro-2-methoxyphenoxy)-methyl]-N-(triphenylmethyl)-1-piperidinepropanamine are suspended in 215 ml of methanol. The reaction mixture is cooled to 0° C. and gaseous hydrochloric acid is bubbled in. The reaction mixture is allowed to return to room temperature and is evaporated to dryness, and the product obtained is recrystallised in an MeOH/AcOEt (50 ml:150 ml) mixture. Yield: 84.9%, M.p. 153°-157° C.

5.3.
2-{[3-{4-[(5-Chloro-2-methoxyphenoxy)methyl]-1-piperidyl}propyl]amino}pyrimidine-4-carboxamide In a 100-ml round-bottomed flask, 4.63 g (0.012 mol) of 4-[(5-chloro-2-methoxyphenoxy)methyl]-1-piperidinepropanamine hydrochloride, 1.85 g (0.012 mol) of 2-chloropyrimidine-4-carboxamide, 5.8 g (0.042 mol) of K$_2$CO$_3$ and 0.2 g of NaI are introduced under argon into 30 ml of DMF.

The reaction mixture is stirred at room temperature for 24 h, poured into 100 ml of water and extracted 3 times with ethyl acetate.

The organic phases are washed with water, dried and evaporated. The product crystallises.

1.06 g of fumaric acid are added to 3.95 g of base dissolved in 50 ml of methanol. The methanol is evaporated off. The product obtained is recrystallised in methanol. Yield: 56.4%. M.p. 178°-180° C.

EXAMPLE 6

2-{[3-{4-[(4,5-Difluoro-2-methoxyphenoxy)methyl]-1-piperidyl}ethyl]amino}pyrimidine-4-carboxamide fumarate

6.1.
4-[(4,5-Difluoro-2-methoxyphenoxy)methyl]-N-(triphenylmethyl)-1-piperidineethanamine 5.88 g (0.020 mol) of 4-[(4,5-difluoro-2-methoxyphenoxy)methyl]piperidine hydrochloride, 7.7 g (0.021 mol) of 2-bromo-N-(triphenylmethyl)ethylamine and 6.91 g (0.050 mol) of K$_2$CO$_3$ in 40 ml of DMF are reacted. The reaction mixture is heated to 90° C. for 8 hours. It is cooled to room temperature, poured into 500 ml of water and extracted 3 times with ethyl acetate. The organic phases are combined, washed with water, dried over MgSO$_4$ and filtered, and the solvent is evaporated off under reduced pressure. The product is obtained in the form of an oil after chromatography. Yield: 41.5%.

6.2.
4-[(4,5-Difluoro-2-methoxyphenoxy)methyl]-1-piperidineethanamine hydrochloride 4.5 g (0.0083 mol) of compound 6.1 are suspended in 100 ml of methanol. The reaction mixture is cooled to 0° C. and gaseous hydrochloric acid is bubbled in. The reaction mixture is heated to the refluxing temperature for 4 hours and then cooled to room temperature. The solvent is evaporated off under reduced pressure, 50 ml of water followed by 100 ml of 30% NaOH are then added to the crude residue and the mixture is extracted with CH$_2$Cl$_2$. The organic phases are combined, washed with water, dried over MgSO$_4$, filtered and evaporated under reduced pressure to obtain 2.1 g (0.070 mol) of oil 6.2. Yield: 84%.

6.3.
2-{[3-{4-[(4,5-Difluoro-2-methoxyphenoxy)methyl]-1-piperidyl}ethyl]amino}pyrimidine-4-carboxamide In a 100-ml round-bottomed flask, 2.1 g (0.007 mol) of compound 6.2, 1.21 g (0.0077 mol) of 2-chloropyrimidine-4-carboxamide, 1.45 g (0.0105 mol) of $K_2CO_3$ and 0.1 g of NaI are introduced into 15 ml of DMF.

The reaction mixture is stirred at room temperature for 24 hours, poured into 100 ml of water and extracted 3 times with ethyl acetate. The organic phases are washed with water, dried over $MgSO_4$ and filtered, and the solvent is evaporated off under reduced pressure. The crude residue is chromatographed on a silica column with a $CH_2Cl_2$/MeOH (98:2 to 92:8) mixture as eluent, to give 1.38 g (0.0033 mol) of base.

0.38 g of fumaric acid is added to 1.38 g of base dissolved in 10 ml of ethanol, and the solvent is then evaporated off under reduced pressure. The product obtained is recrystallised in a methanol/ethanol mixture to obtain 1.35 g (0.0025 mol). Yield: 36%. M.p. 211°–215° C. (decomposition).

EXAMPLE 7

[N-{2-[4-(4-Fluorophenoxy)-1-piperidyl]ethyl}-N-methylamino]pyrimidine-4-carboxamide fumarate

7.1.

4-(4-Fluorophenoxy)-N-(triphenylmethyl)-N-methyl-1-piperidineethylamine

In a 500 ml three-necked flask, 5.25 g (0.0227 mol) of 4-(4-fluorophenoxy)piperidine hydrochloride, 9.5 g (0.025 mol) of 2-bromo-N-(triphenyl-methyl)-N-methylethylamine and 7.85 g (0.0568 mol) of $K_2CO_3$ are introduced into 50 ml of DMF, and the reaction mixture is then heated to 90°–100° C. for 7 hours. It is cooled to room temperature, poured into 200 ml of water and extracted 3 times with ethyl acetate. The organic phases are washed with water, dried over $MgSO_4$ and filtered, and the solvent is then evaporated off under reduced pressure. After chromatography on a silica column with a $CH_2Cl_2$/MeOH (98:2) mixture as eluent, 8 g (0.016 mol) of product are obtained in the form of an oil. Yield: 71.4%.

7.2. N-Methyl-4-(4-fluorophenoxy)-1-piperidineethylamine dihydrochloride.

7.7 g (0.0156 mol) of compound 7.1 are suspended in 160 ml of methanol. The reaction mixture is cooled to 0° C. and gaseous hydrochloric acid is bubbled in. The reaction mixture is heated to the refluxing temperature for 7 hours and then cooled to room temperature. The solvent is evaporated off under reduced pressure and the product is then crystallised by adding ethyl acetate. 4.65 g (0.0143 mol) of dihydrochloride 7.2 are obtained. Yield: 92%. M.p. 212°–214.5° C.

7.3.

[N-{2-[4-(4-Fluorophenoxy)-1-piperidyl]ethyl}-N-methylamino]pyrimidine-4-carboxamide In a 500-ml round-bottomed flask, 4.65 g (0.0143 mol) of hydrochloride 7.2, 2.33 g (0.0148 mol) of 2-chloropyrimidine-4-carboxamide, 6.9 g (0.050 mol) of $K_2CO_3$ and 0.2 g of NaI are introduced under argon into 75 ml of DMF. The reaction mixture is stirred at room temperature for 24 hours, poured into 150 ml of water and extracted three times with ethyl acetate. The organic phases are washed with water, dried over $MgSO_4$ and filtered, and the solvent is then evaporated off under reduced pressure. The product is crystallised by adding ether, to obtain 4.1 g (0.011 mol) of base. 1.28 g of fumaric acid are added to 4.1 g of base dissolved in 200 ml of ethanol, and the mixture is then evaporated under reduced pressure. The product is recrystallised in ethanol to obtain 3.3 g (0.0068 mol). Yield: 47% M.p. 196°–198.5° C.

The following table illustrates compounds of general formula (I) which may be prepared by the process as described above.

TABLE

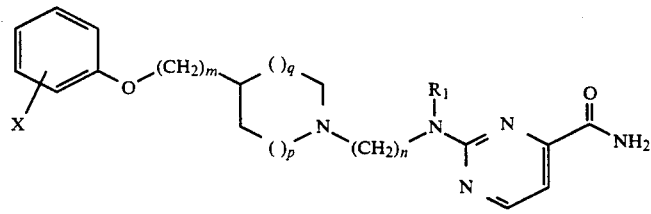

| Compound | X | m | p | q | n | $R_1$ | $[\alpha]_\eta^{25}$ (°) | Salt | M.p. (°C.) |
|---|---|---|---|---|---|---|---|---|---|
| 1 | H | 0 | 0 | 2 | 3 | H | rac | fum | 135–138 |
| 2 | 2-$OCH_3$ | 0 | 0 | 2 | 3 | H | rac | fum | 148–151 |
| 3 | H | 0 | 1 | 1 | 3 | H | rac | fum | 185–187 |
| 4 (Ex. 1) | 4-F | 0 | 1 | 1 | 3 | H | rac | fum | 171–174 |
| 5 | 2-$OCH_3$ | 0 | 1 | 1 | 3 | H | rac | fum | 157–160 |
| 6 | 2-$iC_3H_7$,5-$CH_3$ | 0 | 1 | 1 | 3 | H | rac | fum | 184–187 |
| 7 | 2-$OCH_3$,5-Cl | 0 | 1 | 1 | 3 | H | rac | fum | 199–201 |
| 8 | 2-$OCH_3$,5-F | 0 | 1 | 1 | 3 | H | rac | fum | 191.5–192.5 |
| 9 | 4-F | 0 | 1 | 1 | 2 | H | rac | fum | 245–247.5 |
| 10 (Ex. 7) | 4-F | 0 | 1 | 1 | 2 | $CH_3$ | rac | fum | 196–198.5 |
| 11 | H | 1 | 1 | 1 | 3 | H | rac | ½fum | 190–193 |
| 12 | 2-$OCH_3$ | 1 | 1 | 1 | 3 | H | rac | chl | 198–201 |
| 13 (Ex. 4) | 2-$iC_3H_7$,5-$CH_3$ | 1 | 1 | 1 | 3 | H | rac | fum | 183–188 |
| 14 (Ex. 5) | 2-$OCH_3$,5-Cl | 1 | 1 | 1 | 3 | H | rac | fum* | 178–180 |
| 15 | 2-$OCH_3$,5-F | 1 | 1 | 1 | 3 | H | rac | fum | 167–169 |
| 16 | 2-$OCH_3$,4,5-$(F)_2$ | 1 | 1 | 1 | 3 | H | rac | ½fum | 185–188 |
| 17 | 2-$iC_3H_7$ | 1 | 1 | 1 | 3 | H | rac | fum | 194–196(dec) |
| 18 | 2-$iC_3H_7$,4-F,5-$CH_3$ | 1 | 1 | 1 | 3 | H | rac | fum | 195–198 |
| 19 | 2-$OCH_3$,5-Cl | 1 | 1 | 1 | 2 | H | rac | fum | 228–232(dec) |
| 20 (Ex. 6) | 2-$OCH_3$,4,5-$(F)_2$ | 1 | 1 | 1 | 2 | H | rac | fum | 211–215(dec) |
| 21 | 2-$OCH_3$,4,5-$(F)_2$ | 1 | 1 | 1 | 2 | $CH_3$ | rac | fum | 188–192(dec) |
| 22 (Ex. 2) | H | 1 | 0 | 2 | 3 | H | rac | fum | 144–146 |
| 23 | H | 1 | 0 | 2 | 3 | H | +4,48(c = 1,MeOH) | fum | 150.5–152.5 |
| 24 | H | 1 | 0 | 2 | 3 | H | −6(c = 1,MeOH) | fum | 151–153 |
| 25 (Ex. 3) | 4-F | 1 | 0 | 2 | 3 | H | rac | fum | 150–153 |

TABLE-continued

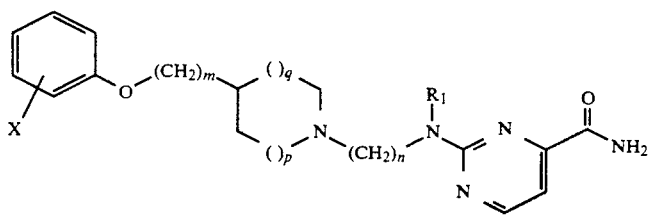

| Compound | X | m | p | q | n | $R_1$ | $[\alpha]_\eta^{25}$ (°) | Salt | M.p. (°C.) |
|---|---|---|---|---|---|---|---|---|---|
| 26 | 2-OCH$_3$ | 1 | 0 | 2 | 3 | H | rac | fum | 137-142 |
| 27 | 2-iC$_3$H$_7$,5-CH$_3$ | 1 | 0 | 2 | 3 | H | rac | fum | 141-148 |
| 28 | 2-OCH$_3$,5-Cl | 1 | 0 | 2 | 3 | H | rac | fum | 139-141 |
| 29 | 2-OCH$_3$,4,5-(F)$_2$ | 1 | 0 | 2 | 3 | H | rac | ½fum | 183-186 |
| 30 | 2-iC$_3$H$_7$,5-CH$_3$ | 1 | 0 | 2 | 3 | CH$_3$ | rac | chl | 138-143 |
| 31 | 4-F | 1 | 0 | 2 | 2 | H | rac | fum | 210-213 |
| 32 | 4-F | 1 | 0 | 2 | 2 | CH$_3$ | rac | fum | 171-173.5 |

Note:
fum denotes a fumarate
½fum denotes a hemifumarate
chl denotes a hydrochloride
fum* denotes a hydrated fumarate
dec denotes decomposition.

The compounds of the invention underwent a series of pharmacological tests which demonstrated their value as substances having therapeutic activity.

The compounds of the invention were subjected to studies of their antagonist activity with respect to the type $\alpha_1$ adrenoceptors in the lower urinary tract.

Their in vitro activity was studied on isolated rabbit urethra.

Rings of adult rabbit urethra are prepared according to the method of Ueda et al., Eur. J. Pharmacol., (1984), 103, 249-254, and then, after sensitisation to noradrenaline, the curve of concentration-response to phenylephrine is determined in the absence and presence of the test compound.

The potency of the $\alpha_1$-adrenergic antagonism of each compound is evaluated by calculating the pA$_2$, the antilogarithm of the molar concentration of antagonist, in the presence of which the agonist concentration must be doubled in order to generate the same effect as in its absence.

The pA$_2$ values of the compounds are of the order of 5.5 to 9.

The in vivo activity of the compounds of the invention was studied in respect of their effect on urethral hypertonia generated by stimulation of the hypogastric nerve in anaesthetised cats.

Adult male cats were anaesthetised with pentobarbitone sodium, and prepared according to the method of Theobald, J. Auton. Pharmac., (1983), 3, 235-239, so as to obtain a urethral hypertonia by stimulation of the sympathetic fibres of the hypogastric nerve. The contractile responses of the urethra to electrical stimulation of the hypogastric nerve are noted before and after intravenous administration of the test compounds at cumulative doses from 1 to 1,000 µg/kg.

The potency of the $\alpha_1$-adrenergic antagonism of each compound is evaluated by calculating the ID$_{50}$, the dose which inhibits urethral hypertonia by 50%.

The ID$_{50}$ values of the compounds of the invention are of the order of 0.01 to 3 mg/kg.

The results of the tests show that some of the compounds of the invention possess in vitro an antagonist activity with respect to the $\alpha_1$-adrenoceptors of the smooth muscles of the lower urinary tract (urethra) when the muscles are stimulated by an $\alpha_1$-adrenergic agonist (phenylephrine). In vivo, they inhibit urethral hypertonia generated by sympathetic nerve stimulation.

The compounds of the invention can hence be used for the symptomatic treatment of diseases and ailments involving hyperactivity of the $\alpha_1$-adrenergic system in the lower urinary tract, and in particular for the treatment of benign hypertrophy of the prostate, dysuria and pollakiuria.

For this purpose, they may formulated as pharmaceutical compositions, in which they are the active ingredient. They can be presented in all forms suited to enteral or parenteral administration, in combination with pharmaceutical excipients, for example in the form of tablets, dragees, capsules including hard gelatin capsules, solutions or suspensions to be taken by mouth or injected, and suppositories, their content being such as to permit a daily dose of 0.5 to 100 mg of active substance.

We claim:

1. A compound which is a 2-aminopyrimidine-4-carboxamide derivative of the formula (I)

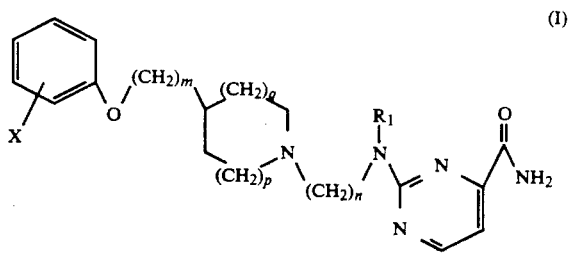

(I)

in which
m is 0 or 1;
p is 0 or 1;
q is 1 or 2;
p+q equals 2;
n is 2 or 3;
$R_1$ represents a hydrogen atom or a methyl group; and X represents at least one substituent selected from hydrogen, fluorine, chlorine, methoxy, methyl and isopropyl;
or a pharmaceutically acceptable acid addition salt thereof.

2. A pharmaceutical composition comprising as active ingredient a compound as claimed in claim 1.

3. A method of treating a disease or ailment directly or indirectly involving the $\alpha_1$-adrenergic receptors which comprises administering to a patient a compound as claimed in claim 1.

4. A pharmaceutical composition for treating disorders and diseases of the lower urinary tract comprising an effective amount of a compound as claimed in claim 1.

5. A method of treating a disease or disorder of the lower urinary tract which comprises administering to a patient an effective amount of a compound as claimed in claim 1.

* * * * *